United States Patent

Fushimi et al.

[11] Patent Number: 5,849,654
[45] Date of Patent: Dec. 15, 1998

[54] CATALYST FOR OLEFIN POLYMERIZATION AND PROCESS FOR PRODUCING POLYOLEFIN USING THE SAME

[75] Inventors: Masaki Fushimi, Oita; Yasushi Kuroda, Kanagawa; Shintaro Inazawa, Oita, all of Japan

[73] Assignee: Japan Polyolefins Co., Ltd., Tokyo, Japan

[21] Appl. No.: 562,958

[22] Filed: Nov. 27, 1995

[30] Foreign Application Priority Data

Nov. 25, 1994 [JP] Japan .................................. 6-291560
Nov. 25, 1994 [JP] Japan .................................. 6-291561
Nov. 28, 1994 [JP] Japan .................................. 6-293225

[51] Int. Cl.⁶ .............................. C08F 4/649; C08F 10/00
[52] U.S. Cl. ........................ 502/125; 526/125.3; 526/351
[58] Field of Search ............................................. 502/125

[56] References Cited

U.S. PATENT DOCUMENTS

| | | | |
|---|---|---|---|
| 4,829,038 | 5/1989 | Hoppin et al. | 502/125 |
| 5,147,839 | 9/1992 | Fujita et al. | 526/119 |
| 5,407,883 | 4/1995 | Fushimi et al. | 502/125 |
| 5,652,303 | 7/1997 | Ishimaru et al. | 526/125.3 |

*Primary Examiner*—Edward J. Smith
*Attorney, Agent, or Firm*—Sughrue, Mion, Zinn, Macpeak & Seas, PLLC

[57] ABSTRACT

A catalyst for olefin polymerization comprising: (A) a solid catalyst component comprising a titanium compound, a magnesium compound, and a halogen compound; (B) an organoaluminum compound; (C) a first organosilicon compound represented by formula (I):

$$(R^1O)_3-Si-\underset{\underset{R^4}{|}}{\overset{\overset{R^2}{|}}{C}}-R^3 \qquad (I)$$

wherein $R^1$ represents a hydrocarbon group having 1 to 4 carbon atoms; $R^2$ represents a hydrocarbon group having 1 to 6 carbon atoms or a hydrogen atom; $R^3$ and $R^4$ each represent a hydrocarbon group having 1 to 6 carbon atoms; and $R^2$, $R^3$, and $R^4$ may be the same or different; and (D) a second organosilicon compound represented by formula (II):

$$(R^5O)_3-Si-CH_2-\underset{\underset{R^8}{|}}{\overset{\overset{R^6}{|}}{C}}-R^7 \qquad (II)$$

wherein $R^5$ represents a hydrocarbon group having 1 to 4 carbon atoms; and $R^6$, $R^7$, and $R^8$, which may be the same or different, each represent a hydrocarbon group having 1 to 6 carbon atoms or a hydrogen atom.

2 Claims, 1 Drawing Sheet

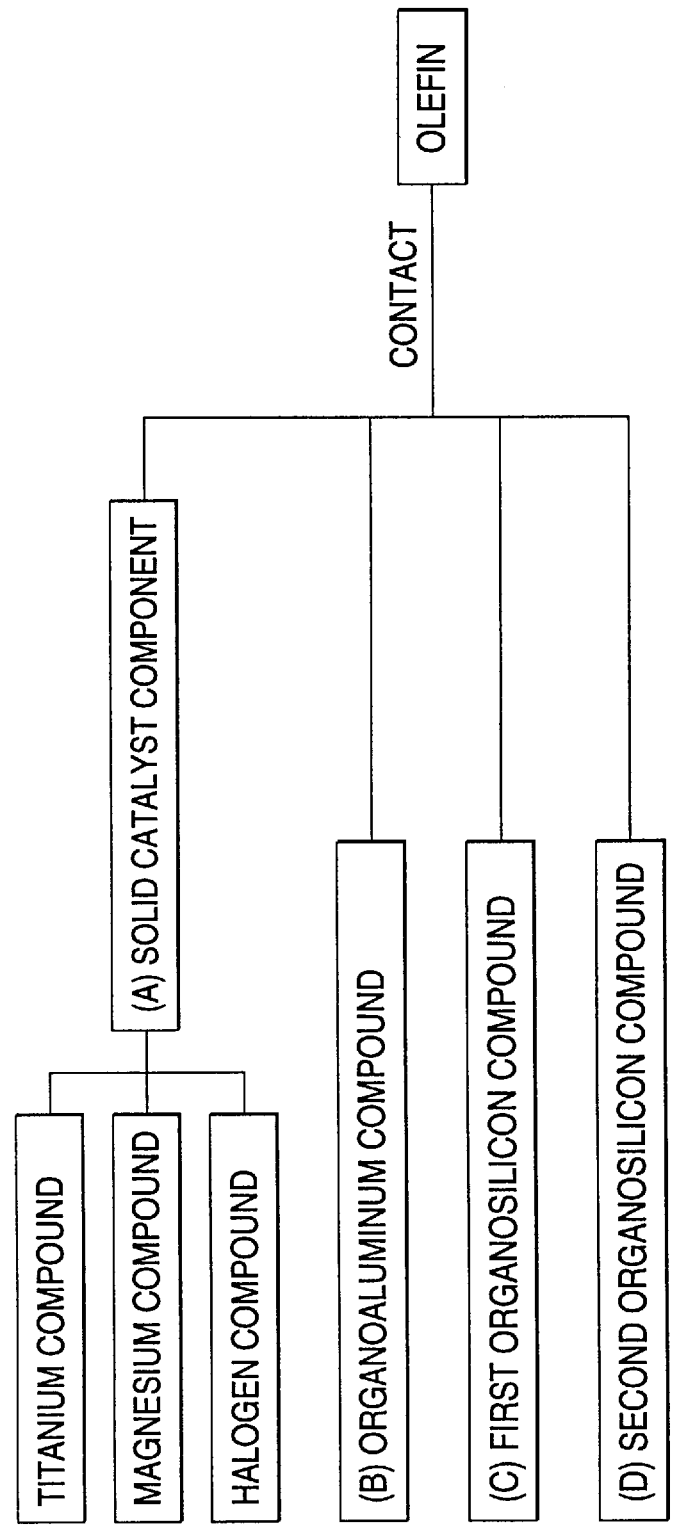

CATALYST FOR OLEFIN POLYMERIZATION AND PROCESS FOR PRODUCING POLYOLEFIN USING THE SAME

FIELD OF THE INVENTION

The present invention relates to a process for producing polyolefins with an extremely low content of low-molecular weight components, particularly components soluble in boiling acetone (hereinafter referred to as "boiling acetone-soluble components") which causes a reduction in rigidity of polyolefins, and to a catalyst to be used in the process. The present invention also relates to a process for producing organosilicon compounds useful as external donor for the above-mentioned catalyst, particularly alkyltrialkoxysilanes, and a process for producing alkyltrichlorosilanes useful as starting material for producing the alkyltrialkoxysilanes.

BACKGROUND OF THE INVENTION

It is known that polymers with improved stereoregularity can be obtained by using an organosilicon compound as a promoter of a Zieglar catalyst-on-carrier. Polyolefins having high stereoregularity can be a highly rigid material and are therefore of considerable utility. While a number of organosilicon compounds have been proposed to date as a promoter leading to high stereoregularity, some involve high production cost, some by-produce substances harmful to humans, and some attain only a low yield of polymers. Only a few organosilicon compounds are practically useful and exhibit satisfactory performance.

Compounds represented by formula (I) shown below are among the available organosilicon compounds that are practical and have satisfactory performance (as described in JP-A-5-287019, the term "JP-A" as used herein means an "unexamined published Japanese patent application"). However, it is received that low-molecular weight components contained in the resulting polyolefins in very small amounts reduce the rigidity of the polyolefins, and polyolefins having a further reduced content of low-molecular weight components have been demanded to meet the recent need of high rigidity materials.

Among the low-molecular weight components, boiling acetone-soluble components are considered particularly causative of the reduction in rigidity. Washing with an organic solvent is a well-known method for removing such low-molecular weight components. However, because washing is costly, it has been demanded to develop a method for removing low-molecular weight components without including a washing step.

Alkyltrialkoxysilanes are known as effective electron donors for Zieglar catalysts. Inter alia, thexyltrialkoxysilanes have extremely high industrial value because polyolefins having high stereoregularity can be obtained by using them as electron donor of a Zieglar catalyst on magnesium chloride, as disclosed in JP-A-5-287019.

Alkyltrichlorosilanes are known as not only raw material for silicone resins and surface treating agents for inorganic substances but also starting material for the above-mentioned alkyltrialkoxysilanes, and their importance has recently been increasing.

Processes for preparing alkyltrichlorosilanes, especially those having a branched alkyl group having 6 carbon atoms (e.g., a thexyl group) are disclosed, e.g., in *Chem. Lett.*, p. 2247 (1987), *J. Am. Chem. Soc.*, Vol. 70, p. 484 (1948), *Chem. Listy.*, Vol. 52, p. 640 (1958), and *Tetrahedron Lett.*, Vol. 26, p. 5511 (1985). These techniques provide alkyltrichlorosilanes either as a single substance or a mixture of structural isomers. In the former case, where a plurality of alkyltrichlorosilanes should be used in combination, other alkyltrichlorosilanes to be combined with an alkyltrichlorosilane obtained as a single substance must be prepared separately. In the latter case, it has been difficult to control the mixing ratio of the isomers being produced.

SUMMARY OF THE INVENTION

An object of the present invention is to provide a process for producing a polyolefin using a Zieglar catalyst on carrier, by which a polyolefin having an extremely low content of low-molecular weight components, especially boiling acetone-soluble components, can be obtained without involving a washing step.

Another object of the present invention is to provide a process for preparing an alkyltrialkoxysilane containing a thexyltrialkoxysilane (i.e., 2,3-dimethyl-isobutyltrialkoxysilane or, according to IUPAC nomenclature, 2,3-dimethyl-2-trialkoxysilylbutane), which is an effective electron donor of a Zieglar catalyst, by controlling the production ratio of structural isomers.

A further object of the present invention is to provide a process for preparing an alkyltrichlorosilane containing thexyltrichlorosilane (i.e., 1,1-dimethyl-isobutyltrichlorosilane or, according to IUPAC nomenclature, 2,3-dimethyl-2-trichlorosilylbutane), which is a starting material for alkyltrialkoxysilanes useful as electron donor of a Zieglar catalyst, by controlling the production ratio of structural isomers.

Other objects and effects of the present invention will be apparent from the following description.

In order to accomplish these objects, the inventors of the present invention have conducted extensive study on the promoter to be used for a Zieglar catalyst supported on a carrier, particularly an electron donor (external donor) to be added to a polymerization system. The inventors have found as a result that polymers with an extremely reduced content of boiling acetone-soluble components can be obtained by using, as external donor, a plurality of organosilicon compounds having a specific structure.

They have also found that alkyltrialkoxysilanes, which can be used as the aforesaid plurality of organosilicon compounds having a specific structure, can be obtained while controlling the production ratio of structural isomers by reacting a mixture of 2,3-dimethyl-2-butene and 2,3-dimethyl-1-butene with trichlorosilane to prepare corresponding alkyltrichlorosilanes and further reacting the resulting alkyltrichlorosilanes and an alcohol component.

The present invention relates to a catalyst for olefin polymerization comprising:

(A) a solid catalyst component comprising a titanium compound, a magnesium compound, and a halogen compound;

(B) an organoaluminum compound;

(C) a first organosilicon compound represented by formula (I):

wherein $R^1$ represents a hydrocarbon group having 1 to 4 carbon atoms; $R^2$ represents a hydrocarbon group having 1 to 6 carbon atoms or a hydrogen atom; $R^3$ and $R^4$ each represent a hydrocarbon group having 1 to 6 carbon atoms; and $R^2$, $R^3$, and $R^4$ may be the same or different; and (D) a second organosilicon compound represented by formula (II):

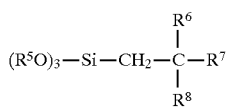

$$(R^5O)_3-Si-CH_2-\underset{R^8}{\overset{R^6}{\underset{|}{\overset{|}{C}}}}-R^7 \quad (II)$$

wherein $R^5$ represents a hydrocarbon group having 1 to 4 carbon atoms; and $R^6$, $R^7$, and $R^8$, which may be the same or different, each represent a hydrocarbon group having 1 to 6 carbon atoms or a hydrogen atom.

The present invention also relates to a process for producing a polyolefin, which comprises polymerizing an olefin in the presence of the above-mentioned catalyst.

The present invention further relates to a process for producing an alkyltrialkoxysilane, which comprises reacting (E) a solution containing thexyltrichlorosilane which is obtained by reacting a mixture comprising 2,3-dimethyl-2-butene and 2,3-dimethyl-1-butene with trichlorosilane in the presence of a catalyst, and (F) an alcohol, in the presence of a neutralizing agent with or without a solvent.

The present invention furthermore relates to a process for producing an alkyltrichlorosilane, which comprises reacting a mixture of 2,3-dimethyl-2-butene and 2,3-dimethyl-1-butene with trichlorosilane in the presence of a catalyst.

BRIEF DESCRIPTION OF THE DRAWING

FIG. 1 is a flow chart illustrating the production of a polyolefin according to the present invention.

DETAILED DESCRIPTION OF THE INVENTION

The effects of the present invention are obtained by using a plurality of organosilicon compounds having a specific structure in combination as external donor. While not clear, it is considered from various phenomena that the active sites which would have produced low-molecular weight components are poisoned with component (D) (the second organosilicon compound represented by formula (II)) added in a small amount or the active sites are converted to those generating high-molecular weight components.

Examples of the magnesium compound which can be used in the present invention includes magnesium halides, such as magnesium chloride and magnesium bromide; magnesium alkoxides, such as magnesium ethoxide and magnesium isopropoxide; magnesium carboxylates, such as magnesium laurate and magnesium stearate; and alkylmagnesiums, such as butylethylmagnesium. These magnesium compounds may be used either individually or as a mixture of two or more thereof. Magnesium halides or precursors thereof capable of forming a magnesium halide in the preparation of a catalyst are preferred. Magnesium chloride or precursors thereof are still preferred.

Examples of the titanium compound which can be used in the present invention includes titanium halides, such as titanium tetrachloride and titanium trichloride; titanium alkoxides, such a s titanium butoxide and titanium ethoxide; and alkoxytitanium halides, such as phenoxytitanium chloride. These titanium compounds may be used either individually or as a mixture of two or more thereof.

Examples of the halogen compound which can be used in the present invention includes compounds containing fluorine, chlorine, bromine or iodine, preferably chlorine. Typical examples are titanium halides, such as titanium tetrachloride and titanium tetrabromide; silicon halides, such as silicon tetrachloride and silicon tetrabromide; and phosphorus halides, such as phosphorus trichloride and phosphorus pentachloride. Depending on the process-of-use for preparing the catalyst, halogenated hydrocarbons, halogen molecules or hydrohalogenic acids (e.g., HCl, HBr or HI) may serve. The halogen compound may be used in common to the titanium compound or magnesium compound.

Various electron donors (internal donors) may be, and are preferably, used for the preparation of solid catalyst component (A). Examples of the electron donors include oxygen-containing compounds and nitrogen-containing compounds. Specific examples of the electron donors include:

(i) alcohols having 1 to 20 carbon atoms, such as methanol, ethanol, propanol, butanol, heptanol, hexanol, octanol, dodecanol, octadecyl alcohol, 2-ethylhexyl alcohol, benzyl alcohol, cumyl alcohol, diphenylmethanol, and triphenylmethanol;

(ii) alkyl-substituted or unsubstituted phenol compounds having 6 to 25 carbon atoms, such as phenol, cresol, ethylphenol, propylphenol, cumylphenol, nonylphenol and naphthol;

(iii) ketones having 3 to 15 carbon atoms, such as acetone, methyl ethyl ketone, methyl isobutyl ketone, acetophenone, and cyclohexanone;

(iv) aldehydes having 2 to 15 carbon atoms, such as acetaldehyde, propionaldehyde, tolualdehyde, and naphthoaldehyde;

(v) organic acid esters having 2 to 20 carbon atoms, such as methyl formate, ethyl formate, methyl acetate, ethyl acetate, propyl acetate, octyl acetate, cyclohexyl acetate, methyl cellosolve acetate, cellosolve acetate, ethyl propionate, methyl n-butyrate, methyl isobutyrate, ethyl isobutyrate, isopropyl isobutyrate, ethyl valerate, butyl valerate, ethyl stearate, methyl chloroacetate, ethyl dichloroacetate, methyl methacrylate, ethyl methacrylate, ethyl crotonate, ethyl cyclohexanecarboxylate, methyl phenylacetate, methyl phenylbutyrate, propyl phenylbutyrate, methyl benzoate, ethyl benzoate, propyl benzoate, butyl benzoate, octyl benzoate, cyclohexyl benzoate, phenyl benzoate, benzyl benzoate, cellosolve benzoate, methyl toluylate, ethyl toluylate, amyl toluylate, ethyl ethylbenzoate, methyl anisate, ethyl anisate, ethyl ethoxybenzoate, diethyl phthalate, diisobutyl phthalate, diheptyl phthalate, dineopentyl phthalate, diethyl malonate, diethyl isopropylisopentylmalonate, diethyl diisobutylmalonate, γ-butyrolactone, γ-valerolactone, coumarin, phthalide, diethyl carbonate, methyl orthoformate, and ethyl orthoformate;

(vi) alkoxy esters, such as methyl methoxyacetate, ethyl methoxyacetate, butyl methoxyacetate, phenyl methoxyacetate, methyl ethoxyacetate, ethyl ethoxyacetate, butyl ethoxyacetate, phenyl ethoxyacetate, ethyl n-propoxyacetate, ethyl isopropoxyacetate, methyl n-butoxyacetate, ethyl isobutoxyacetate, ethyl n-hexyloxyacetate, octyl sec-hexyloxyacetate, methyl 2-methylcyclohexyloxyacetate, methyl 3-methoxypropionate, ethyl 3-methoxypropionate, butyl 3-methoxypropionate, ethyl 3-ethoxypropionate, butyl 3-ethoxypropionate, n-octyl 3-ethoxypropionate, dodecyl 3-ethoxypropionate, pentamethylphenyl 3-ethoxypropionate, ethyl 3-(isopropoxy)propionate, butyl 3-(isopropoxy)propionate, allyl 3-(n-propoxy) propionate, cyclohexyl 3-(n-butoxy)propionate, ethyl 3-neopentyloxypropionate, butyl 3-(n-octyloxy) propionate, octyl 3-(2,6-dimethyldecyloxy)propionate, ethyl 4-ethoxyacetate, cyclohexyl 4-ethoxybutyrate, octyl 5-(n-propoxy)valerate, ethyl 12-ethoxylaurate, ethyl 3-(1-indenoxy)propionate, methyl 3-methoxyacrylate, methyl 2-ethoxyacrylate, ethyl 3-phenoxyacrylate, ethyl 2-methoxypropionate, n-butyl 2-(isopropoxy)butyrate, methyl 2-ethoxyisobutyrate, phenyl 2-cyclohexyloxyisovalerate, butyl 2-ethoxy-2-phenylacetate, allyl 3-neopentyloxybutyrate, methyl 3-ethoxy-3-(o-methylphenyl)propionate, ethyl 3-ethoxy-2-(o-methylphenyl)propionate, ethyl 4-ethoxy-2-methyl-1-naphthylnonanoate, ethyl 2-methoxycyclopentanecarboxylate, butyl 2-ethoxycyclohexanecarboxylate, isopropyl 3-(ethoxymethyl)tetralin-2-acetate, ethyl 8-butoxy-decalin-1-carboxylate, methyl 3-ethoxynorbornane-2-carboxylate, methyl 2-(phenoxy)acetate, ethyl 3-(p-cresoxy)propionate, methyl 4-(2-naphthoxy)butyrate, butyl 5-carbaroxyvalerate, methyl 2-phenoxypropionate, ethyl 3-(4-methylphenoxy)-2-phenylpropionate, ethyl 2-phenoxycyclohexanecarboxylate, ethyl thiophen-3-oxyacetate, ethyl 2-(2-picolinoxymethyl)-cyclohexanecarboxylate, and ethyl 3-furfuryloxypropionate;

(vii) keto esters, such as methyl acetylacetate, ethyl acetylacetate, butyl acetylacetate, methyl propionylacetate, phenyl acetylacetate, ethyl propionylacetate, ethyl propionylacetate, phenyl propionylacetate, butyl propionylacetate, ethyl butyrylacetate, ethyl isobutanoylacetate, ethyl pentanoylacetate, methyl 3-acetylpropionate, ethyl 3-acetylpropionate, butyl 3-acetylpropionate, ethyl 3-propionylpropionate, butyl 3-propionylpropionate, n-octyl 3-propionylpropionate, dodecyl 3-propionylpropionate, pentamethylphenyl 3-propionylpropionate, ethyl 3-(isopropionyl) propionate, butyl 3-(isopropionyl)propionate, allyl 3-(isopropionyl)propionate, cyclohexyl 3-(isopropionyl)propionate, ethyl 3-neopentanoylpropionate, butyl 3-n-laurylpropionate, methyl 3-(2,6-dimethylhexanoyl)propionate, ethyl 4-propionylbutyrate, cyclohexyl 4-propionylbutyrate, octyl 5-butyrylvalerate, ethyl 12-butyryllaurate, methyl 3-acetylacrylate, methyl 2-acetylacrylate, ethyl 3-benzoylpropionate, methyl 3-benzoylpropionate, ethyl 3-methylbenzoylpropionate, butyl 3-toluylbutyrate, ethyl o-benzoylbenzoate, ethyl m-benzoylbenzoate, ethyl p-benzoylbenzoate, butyl o-toluylbenzoate, ethyl o-toluylbenzoate, ethyl m-toluylbenzoate, ethyl p-toluylbenzoate, ethyl o-(2,4,6-trimethylbenzoyl)benzoate, ethyl m-(2,4,6-trimethylbenzoyl)benzoate, ethyl p-(2,4,6-trimethylbenzoyl)benzoate, ethyl o-ethylbenzoylbenzoate, ethyl o-acetylbenzoate, ethyl o-propionylbenzoate, ethyl o-laurylbenzoate, ethyl o-cyclohexanoylbenzoate, and ethyl o-dodecylbenzoate;

(viii) inorganic acid esters, such as methyl borate, butyl titanate, butyl phosphate, diethyl phosphite, and diphenyl phosphorochloridate;

(ix) ethers having 2 to 25 carbon atoms, such as methyl ether, ethyl ether, isopropyl ether, butyl ether, amyl ether, tetrahydrofuran, anisole, diphenyl ether, ethylene glycol diethyl ether, ethylene glycol diphenyl ether, 2,2-dimethoxypropane, 1,3-dimethoxypropane, 1,3-diethoxypropane, 2-isopropyl-2-isopentyl-1,3-dimethoxypropane, and 2,2-diisobutyl-1,3-dimethoxypropane;

(x) acid amides having 2 to 20 carbon atoms, such as acetamide, benzamide, and toluamide;

(xi) acid halides having 2 to 20 carbon atoms, such as acetyl chloride, benzoyl chloride, toluyl chloride, anisic acid chloride, phthaloyl chloride, and phthaloyl isochloride;

(xii) acid anhydrides having 2 to 20 carbon atoms, such as acetic anhydride and phthalic anhydride;

(xiii) amines having 1 to 20 carbon atoms, such as monomethylamine, monoethylamine, diethylamine, tributylamine, piperidine, tribenzylamine, aniline, pyridine, picoline, and tetramethylethylenediamine, (xiv) nitriles having 2 to 20 carbon atoms, such as acetonitrile, benzonitrile, and tolunitrile;

(xv) thiols having 2 to 20 carbon atoms, such as ethyl thioalcohol, butyl thioalcohol, and phenylthiol;

(xvi) thioethers having 4 to 25 carbon atoms, such as diethyl thioether and diphenyl thioether;

(xvii) sulfuric esters having 2 to 20 carbon atoms, such as dimethyl sulfate and diethyl sulfate;

(xviii) sulfonic acids having 2 to 20 carbon atoms, such as phenylmethylsulfone and diphenylsulfone; and (xix) silicon-containing compounds having 2 to 24 carbon atoms, such as phenyltrimethoxysilane, phenyltriethoxysilane, phenyltributoxysilane, vinyltriethoxysilane, diphenyldiethoxysilane, phenyldimethylmethoxysilane, phenyldimethylethoxysilane, triphenylmethoxysilane, hexamethyldisiloxane, octamethyltrisioloxane, trimethylsilanol, phenyldimethylsilanol, triphenylsilanol, diphenylsilanediol, and silicic acid lower alkyl esters (especially ethyl silicate).

These electron donors may be used either individually or as a mixture of two or more thereof. Preferred among them are organic acid esters, alkoxy esters, and keto esters.

The method for preparing the solid catalyst component is not particularly limited. Examples thereof include:

a method comprising bringing a magnesium halide, a titanium halide, and an electron donor into contact by co-grinding or dispersing or dissolving in a solvent;

a method comprising preparing a complex of a magnesium halide and an organic or inorganic compound, which may further contain an electron donor, and bringing the complex into contact with a titanium halide or a complex of a titanium halide an d an electron donor;

a method comprising preparing a complex of a magnesium halide and an organic or inorganic compound, which may further contain an electron donor, and bringing the complex into contact successively with an electron donor and a titanium compound in this order or in the reverse order; and a method comprising bringing a magnesium compound or a combination of a magnesium compound and a titanium compound into contact with an electron donor and, at the same time or thereafter, bringing the system into contact with a titanium compound and/or subjecting the system to halogenation, provided that the titanium compound be used in any of the above steps.

The solid catalyst may be supported on or infiltrated in a substance generally used as a catalyst carrier, such as silica or alumina.

While the proportions of the compounds constituting component (A) are arbitrary as long as the effects of the present invention are recognized, it is generally recommended that the molar ratio of magnesium to titanium ranges from 0.1 to 1,000, preferably 2 to 200; the molar ratio of halogen to titanium ranges from 1 to 100; and the molar ratio of electron donor, if used, to titanium is generally not more than 10, preferably ranges from 0.1 to 5.

While arbitrary as long as the effects of the present invention are recognized, the average particle size of the solid catalyst component is generally 0.1 to 200 μm, preferably 1 to 100 μm, still preferably 10 to 100 μm.

Examples of the organoaluminum compound which can be used in the present invention typically includes those represented by formula (III) to (V):

$$AlR^9R^{10}R^{11} \tag{III}$$

$$R^{12}R^{13}Al-O-AlR^{14}R^{15} \tag{IV}$$

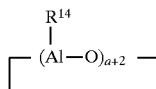

and/or (V)

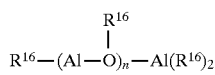

wherein $R^9$, $R^{10}$, and $R^{11}$, which may be the same or different, each represent a hydrocarbon group having at least 12 carbon atoms; $R^{12}$, $R^{13}$, $R^{14}$, and $R^{15}$, which may be the same or different, each represent a hydrocarbon group having at least 12 carbon atoms; $R^{16}$ represents a hydrocarbon group having at least 12 carbon atoms; and n represents an integer of 1 or more.

Typical examples of the organoaluminum compound of formula (III) include a trialkylaluminum, such as trimethylaluminum, triethylaluminum, tripropylaluminum, tributylaluminum, trihexylaluminum, and trioctylaluminum; an alkylaluminum hydride, such as diethylaluminum hydride and diisobutylaluminum hydride; and an alkylaluminum halide, such as diethylaluminum chloride, diethylaluminum bromide, and ethylaluminum sesquichloride.

Typical examples of the organoaluminum compound of formula (IV) include alkyldialuminoxanes, such as tetraethyldialuminoxane and tetrabutyldialuminoxane.

Compounds represented by formula (V) are aluminoxanes, polymers of an aluminum compound. Examples of the group represented by $R^{16}$ includes methyl, ethyl, propyl, butyl or benzyl groups, with methyl and ethyl groups being preferred. n is preferably 1 to 10.

Among these organoaluminum compounds a trialkylaluminum, an alkylaluminum hydride, and an alkylaluminoxane are preferred for their producing favorable results.

The organoaluminum compound is used in the olefin polymerization system in a concentration generally of at least $10^{-4}$ mmol/l, preferably not less than $10^{-2}$ mmol/l, and at a molar ratio generally of at least 0.5, preferably 2 or more, still preferably 10 or more, to the titanium atom in the solid catalyst component. If the amount of the organoaluminum compound is too small, a great reduction in polymerization activity tends to result. Even if the amount of the organoaluminum compound in the polymerization system is increased over 20 mmol/l and over a molar ratio of 1,000 to titanium, no further improvement in catalyst performance results.

Component (C) is the first organosilicon compound represented by formula (I):

wherein $R^1$ represents a hydrocarbon group having 1 to 4 carbon atoms; $R^2$ represents a hydrocarbon group having 1 to 6 carbon atoms or a hydrogen atom; $R^3$ and $R^4$ each represent a hydrocarbon group having 1 to 6 carbon atoms; and $R^2$, $R^3$, and $R^4$ may be the same or different.

Specific examples of the compound represented by formula (I) include isopropyltrimethoxysilane, isopropyltriethoxysilane, isopropyltripropoxysilane, isopropyltriisopropoxysilane, t-butyltrimethoxysilane, t-butyltriethoxysilane, t-butyltripropoxysilane, t-butyltriisopropoxysilane, thexyltrimethoxysilane (i.e., 2,3-dimethyl-2-trimethoxysilylbutane), thexyltriethoxysilane, thexyltripropoxysilane, thexyltriisopropoxysilane, 2,3-dimethyl-2-trimethoxysilylpentane, 2,3-dimethyl-2-triethoxysilylpentane, 2,3-dimethyl-2-tripropoxysilylpentane, 2,3-dimethyl-2-triisopropoxysilylpentane, 2-methyl-3-ethyl-2-trimethoxysilylpentane, 2-methyl-3-ethyl-2-triethoxysilylpentane, 2-methyl-3-ethyl-2-tripropoxysilylpentane, 2-methyl-3-ethyl-2-triisopropoxysilylpentane, 2,3,4-trimethyl-2-trimethoxysilylpentane, 2,3,4-trimethyl-2-triethoxysilylpentane, 2,3,4-trimethyl-2-tripropoxysilylpentane, 2,3,4-trimethyl-2-triisopropoxysilylpentane, 2,3-dimethyl-2-trimethoxysilylhexane, 2,3-dimethyl-2-triethoxysilylhexane, 2,3-dimethyl-2-tripropoxysilylhexane, 2,3-dimethyl-2-triisopropoxysilylhexane, 2,3-dimethyl-3-ethyl-2-trimethoxysilylpentane, 2,3-dimethyl-3-ethyl-2-triethoxysilylpentane, 2,4-dimethyl-3-ethyl-2-trimethoxysilylpentane, 2,4-dimethyl-3-ethyl-2-triethoxysilylpentane, 2,4-dimethyl-3-ethyl-2-tripropoxysilylpentane, 2,4-dimethyl-3-ethyl-2-triisopropoxysilylpentane, 2,4-dimethyl-3-isopropyl-2-trimethoxysilylpentane, 2,4-dimethyl-3-isopropyl-2-triethoxysilylpentane, 2,4-dimethyl-3-isopropyl-2-tripropoxysilylpentane, and 2,4-dimethyl-3-isopropyl-2-triisopropoxysilylpentane. Thexyltrimethoxysilane is particularly preferred.

Component (C) is preferably used at a molar ratio of component (C) to component (B) of 0.001 to 5, still preferably 0.01 to 1.

Component (D) is the second organosilicon compound represented by formula (II):

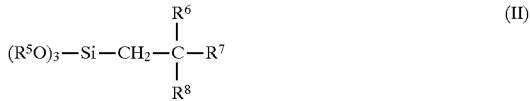

wherein $R^5$ represents a hydrocarbon group having 1 to 4 carbon atoms; and $R^6$, $R^7$, and $R^8$, which may be the same or different, each represent a hydrocarbon group having 1 to 6 carbon atoms or a hydrogen atom.

Specific examples of the compound represented by formula (II) include n-propyltrimethoxysilane, n-propyltriethoxysilane, n-propyltripropoxysilane, n-propyltriisopropoxysilane, n-butyltrimethoxysilane, n-butyltriethoxysilane, n-butyltripropoxysilane, n-butyltriisopropoxysilane, 2,3-dimethylbutyltrimethoxysilane, 2,3-dimethylbutyltriethoxysilane, 2,3-dimethylbutyltripropoxysilane, 2,3- dimethylbutyltriisopropoxysilane, 2,3-dimethylpentyltrimethoxysilane, 2,3-dimethylpentyltriethoxysilane, 2,3-dimethylpentyltripropoxysilane, 2,3-dimethylpentyltriisopropoxysilane, 2-methyl-3-ethylpentyltrimethoxysilane, 2-methyl-3-ethylpentyltriethoxysilane, 2-methyl-3-ethylpentyltripropoxysilane, 2-methyl-3-ethylpentyltriisopropoxysilane, 2,3,4-trimethylpentyltrimethoxysilane, 2,3,4-trimethylpentyltriethoxysilane, 2,3,4-trimethylpentyltripropoxysilane, 2,3-trimethylpentyltriisopropoxysilane, 2,3-dimethylhexyltrimethoxysilane, 2,3-dimethylhexyltriethoxysilane, 2,3-dimethylhexyltripropoxysilane, 2,3-dimethylhexyltriisopropoxysilane, 2,4-dimethyl-3-ethylpentyltrimethoxysilane, 2,4-dimethyl-3-ethylpentyltriethoxysilane, 2,4-dimethyl-3-ethylpentyltripropoxysilane, 2,4-dimethyl-3-ethylpentyltriisopropoxysilane, 2,4-dimethyl-3-isopropylpentyltrimethoxysilane, 2,4-dimethyl-3-isopropylpentyltriethoxysilane, 2,4-dimethyl-3-isopropylpentyltripropoxysilane, and 2,4-dimethyl-3-isopropylpentyltriisopropoxysilane.

Component (D) is preferably selected from the structural isomers of component (C). Accordingly, a choice of component (D) is preferably made in relation to the choice of component (C). A particularly preferred combination of components (C) and (D) is thexyltrimethoxysilane as component (C) and 2,3-dimethylbutyltrimethoxysilane (i.e., 2,3-dimethyl-1-trimethoxysilylbutane) as component (D).

Component (D) is preferably used at a molar ratio of component (D) to component (C) of 0.0001 to 0.1, still preferably 0.01 to 0.05.

Components (C) and (D) are not particularly restricted in the manner of their preparation. For example, components (C) and (D) can be synthesized separately, and then mixed at a prescribed ratio to provide a desired mixture. However, where a plurality of external donors are used in practice, a plurality of stock tanks for storing the external donors and a mixing means for uniformly mixing the donors are needed, and a complicated operation is required for controlling the mixing ratio. When alkyltrichlorosilanes are synthesized in accordance with the specific process hereinafter described, and alkyltrialkoxysilanes are then synthesized therefrom in accordance with the specific process hereinafter described, an isomeric mixture of components (C) and (D) can be prepared efficiently at a controlled ratio of components (C) and (D).

The process for producing an alkyltrichlorosilane according to the present invention comprises reacting a mixture of 2,3-dimethyl-2-butene and 2,3-dimethyl-1-butene and trichlorosilane in the presence of a catalyst.

The alkyltrichlorosilanes as produced by the process of the present invention comprises thexyltrichlorosilane.

The proportion of 2,3-dimethyl-1-butene in the mixture of 2,3-dimethyl-2-butene and 2,3-dimethyl-1-butene preferably ranges from 0.1 to 20% by weight, still preferably from 0.1 to 10% by weight.

The reaction between the mixture of 2,3-dimethyl-2-butene and 2,3-dimethyl-1-butene and trichlorosilane can be carried out in a conventional manner. For example, 1 to 10 equivalents, preferably 1.1 to 5 equivalents, of trichlorosilane are added to 1 equivalent of the mixture of 2,3-dimethyl-2-butene and 2,3-dimethyl-1-butene, and the resulting mixture is allowed to react at 30° to 150° C., preferably 30° to 110° C.

The isomer of thexyltrichlorosilane which is contained in the product of the process of the present invention is preferably 2,3-dimethylbutyltrichlorosilane (or 2,3-dimethyl-i-trichlorosilylbutane according to IUPAC nomenclature). The production ratio (contents in the product) of this isomer in the product is preferably 0.05 to 10% by weight, still preferably 0.05 to 5% by weight.

The catalyst used in the process of the present invention is preferably selected from an azo compound, a peroxide, an aluminum halide, and a transition metal complex. An azo compound or a peroxide is preferred. An azo compound is still preferred for industrial use.

As the azo compound, those represented by R—N=N—R are preferred, wherein R preferably represents an alkyl group, e.g., a methyl, ethyl or 1,1,3,3-tetramethylbutyl group, an alkylcyano group, e.g., a cyanomethyl, cyanoethyl, 1-cyano-1-methylethyl or 1-cyano-1-methylpropyl group, an alkyl ether cyano group, e.g., a 1-cyano-1,3-dimethyl-3-methoxybutyl group, or a cyclic alkylcyano group, e.g., a 1-cyanocyclohexyl group. Specific examples of suitable azo compounds are shown below.

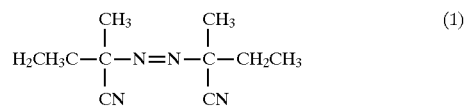 (1)

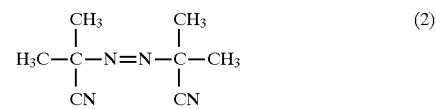 (2)

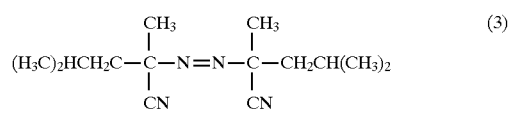 (3)

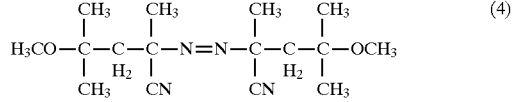 (4)

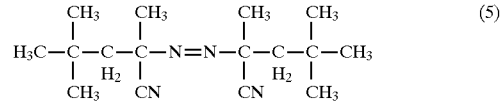 (5)

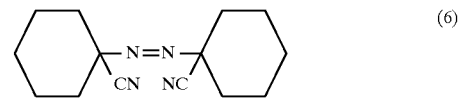 (6)

The azo compound is generally used in an amount of 0.1 to 50 mol % based on the total amount of 2,3-dimethyl-2-butene and 2,3-dimethyl-1-butene. At amounts less than 0.1 mol %, the reaction rate is extremely low. Amounts more than 50 mol % are economically disadvantageous. From the standpoint of reaction rate and yield, a preferred amount is from 0.1 to 10 mol %. At the preferred molar amount, the reaction proceeds quantitatively under the above-mentioned temperature condition to provide a desired alkyltrichlorosilane mixture in a high yield.

If desired, the reaction may be conducted under pressure in an autoclave. In this case, reaction at 50 to 100° C. under 1.1 to 10 atm will provide better results.

The process for producing an alkyltrialkoxysilane according to the present invention comprises reacting (E) a solution containing thexyltrichlorosilane as obtained by the above-mentioned process with (F) an alcohol in the presence of a neutralizing agent with or without a solvent.

The alkyltrialkoxysilanes as obtained by the process of the present invention comprises a thexyltrialkoxysilane.

Component (E) preferably further contains 2,3-dimethylbutyltrichlorosilane (or 2,3-dimethyl-1-trichlorosilylbutane) as an alkyltrichlorosilane other than the predominant product, thexyltrichlorosilane. The 2,3-dimethylbutyltrichlorosilane is preferably present in an amount of 0.05 to 10% by weight, still preferably 0.05 to 5% by weight, based on the total alkyltrichlorosilanes.

The alcohol as component (F) is preferably selected from straight-chain alkyl alcohols having 1 to 6 carbon atoms and branched or cyclic alkyl alcohols having 3 to 6 carbon atoms, for example, methyl alcohol, ethyl alcohol, propyl alcohol, isopropyl alcohol, butyl alcohol, isobutyl alcohol, t-butyl alcohol, or cyclopentyl alcohol.

The reaction of components (E) and (F) may be carried out at a temperature not lower than 20° C., preferably 20° to 150° C., more preferably 30° to 100° C. The reaction may be conducted by stirring the reaction system for not less than 0.5 hour, preferably 0.5 to 30 hours, in the presence of a neutralizing agent with or without a hydrocarbon solvent or an ether solvent.

Component (F) is generally used in an amount of 3 to 4 mol per mole of the total alkyltrichlorosilanes.

Examples of the hydrocarbon solvent, if used, includes benzene, toluene, ethylbenzene, xylene, n-hexane, cyclohexane, and methylcyclohexane. The ether solvent, if used, includes diethyl ether, dibutyl ether, tetrahydrofuran, and dioxane.

Examples of the neutralizing agent to be used includes tertiary amines, such as triethylamine, tripropylamine, tributylamine, and DBU; and urea. The neutralizing agent is generally used in an amount of 3 to 4 mol per mole of the total alkyltrichlorosilanes.

Examples of the alkoxy groups in the alkyltrialkoxysilane produced by the process of the present invention preferably include methoxy, ethoxy, propoxy, butoxy, t-butoxy, and cyclopentoxy groups, with methoxy and ethoxy groups being still preferred, for example, thexyltrimethoxysilane and thexyltriethoxysilane.

Examples of the olefins which can be polymerized by using the above-described catalyst system according to the present invention generally include those containing at least 12 carbon atoms, such as ethylene, propylene, butene-1,4-methylpentene-1, hexene-1, and octene-1. The catalyst of the present invention is especially advantageous for production of stereoregular polymers of an α-olefin having 3 or more carbon atoms, for example, a mixture of the above-enumerated olefins or a mixture of ethylene and other olefins, and particularly propylene or a mixture of propylene and up to about 20 mol % of ethylene or a higher α-olefin. The catalyst is most effective for the production of stereoregular polypropylene.

In carrying out the polymerization, solid catalyst component (A) and organoaluminum compound (B) and, in some cases, organosilicon compounds as components (C) and (D), may be introduced into a polymerization vessel separately, or any two or all of them may previously be mixed. In a typical and preferred mode, an inert solvent (hereinafter described), organoaluminum compound (B), and organosilicon compounds (C) and (D) are added to a dropping funnel having been purged with nitrogen, mixed together, and allowed to stand for a given time (about 1 minute or more); the mixture is brought into contact with solid catalyst component (A); and the mixed system is allowed to react for a given period of time (about 1 minute or more) before it is added to a reaction vessel.

Examples of the inert solvent includes alkanes and cycloalkanes, such as pentane, hexane, heptane, n-octane, isooctane, cyclohexane, and methylcyclohexane; alkyl aromatic hydrocarbons, such as toluene, xylene, ethylbenzene, isopropylbenzene, ethyltoluene, n-propylbenzene, diethylbenzene, and mono- or dialkylnaphthalenes; halogenated or hydrogenated aromatic hydrocarbons, such as chlorobenzene, chloronaphthalene, orthodichlorobenzene, tetrahydronaphthalene, and decahydronaphthalene; high-molecular weight liquid paraffin; and mixtures thereof.

The olefin polymerization can be carried out under a monomer pressure of atmospheric pressure or higher. While a monomer pressure in gas phase polymerization should not below the vapor pressure of the monomer at the polymerization temperature, the monomer pressure usually adopted in the present invention ranges from about 20 to 600 PSI.

The polymerization can be performed either in a liquid phase (such as in an inert solvent or in a liquid monomer (olefin)) or in a gas phase. The reaction mode may be any of a batch system, a semi-continuous system, and a continuous system. The reaction may be carried out in two or more divided stages under varied conditions. For the purpose of ensuring a practical melt flow, a molecular weight regulator, usually hydrogen, may be present in the polymerization system.

The polymerization time is generally from 30 minutes to several hours in the case of a batch system, and a corresponding retention time in the case of a continuous system. In the case of an autoclave reaction system, a reaction time of from about 1 to 6 hours is generally employed. In the case of a slurry system, the reaction time is preferably from 30 minutes to several hours.

Examples of suitable diluent solvents which can be used in slurry polymerization include alkanes or cycloalkanes, such as pentane, hexane, heptane, n-octane, isooctane, cyclohexane and methylcyclohexane; alkyl aromatic hydrocarbons, such as toluene, xylene, ethylbenzene, isopropylbenzene, ethyltoluene, n-propylbenzene, diethylbenzene, and mono- or dialkylnaphthalenes; halogenated or hydrogenated hydrocarbons, such as chlorobenzene, chloronaphthalene, orthodichlorobenzene, tetrahydronaphthalene, and decahydronaphathalene; high-molecular weight liquid paraffin; and mixtures thereof; and others.

In carrying out gas phase polymerization, a stirring tank reactor system, a fluidized bed reactor system, etc. can be used. Typical examples of the system for gas phase olefin polymerization include such a type comprised of a reactor equipped with a stirrer, to which an olefin monomer and catalyst components can be fed. The catalyst components are added either separately or in appropriate combination through at least one opening of the reactor with a regulating valve. The olefin monomer is typically fed to the reactor through a gas recycling system in which a fresh monomer is mixed with the monomer having been withdrawn from the reactor as being unreacted.

Upon completion of the polymerization or if the polymerization must be stopped or the system must be deactivated, though unnecessary in usual operation, a known catalyst poison, such as water, alcohols or acetone, or any other appropriate catalyst deactivator may be added to the reaction system.

The polymerization temperature generally ranges from -10° to 180° C. A range of from 20° to 100° C. is preferred for ensuring satisfactory catalyst performance and a high production rate. A range of from 50° to 80° C. is still preferred.

Preliminary polymerization, which is not always essential but yet preferred, can be carried out using solid catalyst component (A) in combination with at least part of organoaluminum compound (B). An organosilicon compound or an acetal compound may be used in combination. The organosilicon compound referred to here is not limited to the compounds described as components (C) and (D). A preferred concentration of solid catalyst component (A) in the preliminary polymerization system is 0.01 to 200 mmol in terms of titanium per liter of an inert hydrocarbon solvent hereinafter described. Organoaluminum compound (B) is used in the preliminary polymerization system in such an amount that would provide 0.1 to 500 g, preferably 0.1 to 300 g, of a polymer per gram of solid catalyst component (A).

Preliminary polymerization of an olefin monomer is preferably carried out in an inert hydrocarbon solvent in the presence of the above-mentioned catalyst components under milder conditions. Examples of the inert hydrocarbon solvents include aliphatic hydrocarbons, such as propane, butane, pentane, hexane, heptane, octane, decane, dodecane, kerosine; alicyclic hydrocarbons, such as cyclopentane, cyclohexane, and methylcyclopentane; aromatic hydrocarbons, such as benzene, toluene, and xylene; halogenated hydrocarbons, such as ethylene chloride and chlorobenzene; and mixtures thereof. Aliphatic hydrocarbons are especially preferred of them.

The olefin to be preliminarily polymerized may be the same or different from the species to be polymerized subsequently. The preliminary polymerization temperature is decided so that the preliminary polymer being produced may not dissolve in the solvent; such temperature usually ranging from about −10° to 100° C., preferably from −10° to 80° C. A molecular weight regulator, such as hydrogen, may be used in the preliminary polymerization. The preliminary polymerization can be effected in either a batch system or a continuous system.

Use of the catalyst system according to the present invention does not call for any limitation on methods of polymerization control, working-up procedures, and the like, and any conventional techniques known in the art is applicable to the present invention.

The present invention will now be illustrated in greater detail by way of Synthesis Examples and Examples. Unless otherwise indicated, all the percents are by weight.

SYNTHESIS EXAMPLE 1

Synthesis of Alkyltrichlorosilanes

In a 100 ml-volume SUS-made, fluororesin-finished autoclave were charged 22.7 g (0.29 mol) of a mixture of 4% of 2,3-dimethyl-1-butene and the balance of 2,3-dimethyl-2-butene, 54.9 g (0.41 mol) of trichlorosilane, and 0.45 g (0.0027 mol) of 2,2-azobis(isobutyronitrile) as a catalyst. The mixture was allowed to react at 80° C. under 5 atm for 30 hours. After completion of the reaction, the reaction mixture was distilled to recover 47.5 g of a liquid, which was identified to be a 98/2 (by mole) mixture of thexyltrichlorosilane and 2,3-dimethylbutyltrichlorosilane as a result of gas chromatography, mass spectrometry (chemical ion method), and $^1$H-NMR spectroscopy ($CCl_4$, 400 MHz; 2.3–2.7 (m), 2.1–1.6 (m), 1.25 (s), 1.13 (d), 1.5–0.8 (m)).

Comparative Synthesis Example 1

In a 100 ml-volume SUS-made, fluororesin-finished autoclave were charged 22.7 g (0.27 mol) of 2,3-dimethyl-2-butene, 54.9 g (0.41 mol) of trichlorosilane, and 0.45 g (0.0027 mol) of 2,2-azobis(isobutyronitrile) as a catalyst. The mixture was allowed to react at 80° C. under 5 atm. for 30 hours. After completion of the reaction, the reaction mixture was distilled to recover 37.7 g of a liquid, which was identified to be thexyltrichlorosilane as a result of gas chromatography and mass spectrometry (chemical ion method).

SYNTHESIS EXAMPLE 2

Synthesis of Alkyltrimethoxysilanes

In a 500 ml-volume three-necked flask equipped with a stirrer, a Dimroth condenser, and a dropping funnel were charged 21.2 g (0.66 mol) of methanol and 39.6 g (0.66 mol) of urea, and 40.0 g (0.182 mol) of the liquid obtained in Synthesis Example 1 was added from the dropping funnel over a period of 0.5 hour. After the addition, the mixture was stirred at room temperature for 1 hour. The contents of the flask were heated at 70° C. for 6 hours with stirring. After completion of the reaction, the reaction mixture was allowed to stand for phase separation, and the lower layer was discarded. The upper organic layer was distilled to obtain 26.6 g (0.130 mol) of a colorless liquid.

As a result of gas chromatography, mass spectrometry (chemical ion method), and $^1$H-NMR spectroscopy ($CCl_4$, 400 MHz; 2.3–2.7 (m), 2.1–1.6 (m), 1.25 (s), 1.13 (d), 1.5–0.8 (m)), the resulting liquid was identified to be a 98/2 (by mole) mixture of thexyltrimethoxysilane and 2,3-dimethylbutyltrimethoxysilane.

In the following Examples and Comparative Examples, the properties of polymers produced were measured as follows.

1) Boiling acetone-soluble components (A-sol)

A polymer produced was dried in vacuo in a vacuum oven at 60° C. for at least 8 hours. An aliquot weighed out of the dried sample was extracted with boiling acetone in a Soxhlet extractor for 6 hours. The polymer was again dried sufficiently in a vacuum oven and weighed. A-sol (%) was calculated according to the following equation:

$$A\text{-}sol\ (\%) = \frac{Wb - Wa}{Wb} \times 100$$

wherein Wb represents the weight of polymer before extraction (g), and Wa represents the weight of polymer after extraction (g).

2) Polymerization activity

A polymerization activity was calculated according to the following equation:

$$\text{Polymerization Activity (g/g}\cdot\text{h)} = \frac{GWp}{GWc \times T}$$

wherein GWp represents the number of grams of polymer, GWc represents the number of grams of solid catalyst, and T represents the polymerization time.

3) Melt flow rate (MFR; load: 2.16 kg)

Measured in accordance with JIS K-6758-1968.

4) Flexural modulus (FM)

Measured in accordance with ASTM-D-790-66.

All the reagents used in the preparation of solid catalyst components and olefin polymerization (organic solvents, olefins, hydrogen, titanium compounds, magnesium compounds, silicon compounds, etc.) were substantially free from water. The preparation of solid catalyst components and olefin polymerization were all conducted in a water-free nitrogen atmosphere. The organoaluminum compounds and the organosilicon compounds used in the polymerization were used as 1.0M/l hexane solutions and 0.1M/l hexane solutions, respectively.

EXAMPLE 1

Preparation of Solid Ti Catalyst Component (A)

Anhydrous magnesium chloride (1.71 g), 9 ml of decane, and 8.4 ml of 2-ethylhexyl alcohol were heated at 130° C. for 3 hours to prepare a uniform solution. To the solution was added 0.39 g of phthalic anhydride, followed by stirring at 130° C. for 2 hours to dissolve the phthalic anhydride in the solution. The resulting uniform solution A was cooled to room temperature and added dropwise to 72 ml of titanium tetrachloride kept at −20° C. over a period of 1 hour. After the addition, the mixture was heated up to 110° C. taking 4 hours, and upon reaching 110° C., 0.95 g of diisobutyl phthalate was added thereto, followed by stirring for 2 hours at that temperature. After completion of the reaction, the reaction mixture was filtered while hot, the collected solid was suspended in 72 ml of titanium tetrachloride, the suspension was further heated at 110° C. for another 2 hours, and the reaction mixture was filtered while hot. The collected solid was thoroughly washed with decane and hexane until no free titanium compound was detected from the washing, and then dried under reduced pressure.

Polymerization

In a 1.5 l-volume stainless steel-made autoclave were put 5.8 mg of the solid component above prepared, 5.4 mg of thexyltrimethoxysilane (0.8 ml of a 0.1M/l hexane solution), 0.11 mg of 2,3-dimethylbutyltrimethoxysilane (0.8 ml of a 2.0 mM/l hexane solution), and 91 mg of triethylaluminum (0.8 ml of a 1M/l hexane solution). Then, 340 g of propylene and 0.03 g of hydrogen were fed to the autoclave.

The autoclave was heated to keep the inner temperature at 80° C. One hour later, the gas was liberated to terminate the polymerization. The reaction results are shown in Table 1 below.

EXAMPLES 2 TO 4 AND COMPARATIVE EXAMPLES 1 AND 2

Preparation of a solid catalyst component and olefin polymerization were carried out in the same manner as in Example 1, except for changing the kinds of catalyst component (C) and/or catalyst component (D) as shown in Table 1. The reaction results are shown in Table 1.

EXAMPLE 5

Preparation of Solid Ti Catalyst Component (A)

In a thoroughly dried 300 ml-volume round flask were charged 5 g of diethoxymagnesium, 1.22 g of ethyl 3-ethoxy-2-phenylpropionate, and 25 ml of methylene chloride in a nitrogen stream, and the mixture was stirred under reflux for 1 hour. The resulting suspension was added under pressure to 200 ml of titanium tetrachloride kept at room temperature. The mixture was gradually heated up to 110° C. and stirred at that temperature for 2 hours. After completion of the reaction, the precipitated solid was collected by filtration and washed with three 200 ml portions of n-decane at 110° C. To the solid was added 200 ml of titanium tetrachloride, followed by further reacting at 120° C. for 2 hours. The precipitated solid was collected by filtration, washed with three 200 ml portions of n-decane, and then with n-hexane until no chloride ion was detected from the washing.

Polymerization

In a 1.5 l-volume stainless steel-made autoclave were put 2.3 mg of the solid component above prepared, 5.4 mg of thexyltrimethoxysilane (0.8 ml of a 0.1M/l hexane solution), 0.11 mg of 2,3-dimethylbutyltrimethoxysilane (0.8 ml of a 2.0 mM/l hexane solution), and 91 mg of triethylaluminum (0.8 ml of a 1M/l hexane solution). Then, 340 g of propylene and 0.03 g of hydrogen were fed to the autoclave.

The autoclave was heated to keep the inner temperature at 80° C. One hour later, the gas was liberated to terminate the polymerization. The reaction results are shown in Table 1 below.

COMPARATIVE EXAMPLE 3

Preparation of a solid catalyst component and olefin polymerization were carried out in the same manner as in Example 1, except for using no catalyst component (D). The reaction results are shown in Table 1.

EXAMPLE 6

Preparation of Solid Ti Catalyst Component (A)

A suspension was prepared from 12.8 g of metallic magnesium, 88 ml (0.53 mol) of ethyl orthoformate, and 0.5 ml of 1,2-dibromoethane (reaction initiator). To the suspension kept at 55° C. was added a 5 ml portion of a solution of 80 ml (0.80 mol) of n-butyl chloride in 100 ml of hexane, followed by stirring for 50 minutes. Then, the rest of the n-butylchloride solution was added dropwise over 80 minutes, followed by stirring at 70° C. for 4 hours to obtain a solid product. The product was washed 6 times with hexane at 50° C.

The solid product (6.3 g) and 50 ml of decane were put in a reactor, and a mixed solution of 2.0 ml of 2,2,2-trichloroethanol and 11 ml of decane was added thereto dropwise over 30 minutes. After the addition, the mixture was stirred at 80° C. for 1 hour. The solid was collected by filtration, washed successively with four 100 ml portions of hexane and two 100 ml portions of toluene.

To the resulting solid were added 40 ml of toluene and 60 ml of titanium tetrachloride, and the mixture was heated to 90° C., at which a solution of 2.04 g (0.0075 mol) of diethyl isopropylisopentylmalonate in 5 ml of toluene was added thereto over 5 minutes, followed by stirring at 120° C. for 2 hours. The solid was separated by filtration at 90° C. and washed twice with 90° C. toluene. To the solid were added 40 ml of toluene and 60 ml of titanium tetrachloride, and the mixture was stirred at 120° C. for 2 hours, followed by filtration at 110° C. The collected solid was washed with seven 100 ml portions of hexane at room temperature to give a solid titanium catalyst component.

Polymerization

In a 1.5 l-volume stainless steel-made autoclave were put 4.0 mg of the solid component above prepared, 5.4 mg of thexyltrimethoxysilane (0.8 ml of a 0.1M/l hexane solution), 0.11 mg of 2,3-dimethylbutyltrimethoxysilane (0.8 ml of a 2.0 mM/l hexane solution), and 91 mg of triethylaluminum (0.8 ml of a 1M/l hexane solution). Then, 340 g of propylene and 0.03 g of hydrogen were fed to the autoclave.

The autoclave was heated to keep the inner temperature at 80° C. One hour later, the gas was liberated to terminate the polymerization. The reaction results are shown in Table 1 below.

COMPARATIVE EXAMPLE 4

Preparation of a solid catalyst component and olefin polymerization were carried out in the same manner as in Example 1, except for using no catalyst component (D). The reaction results are shown in Table 1.

TABLE 1

| Example No. | Component (C) Kind | Component (C) Amount (mg) | Component (D) Kind | Component (D) Amount (mg) | Polymerization Activity (g/g·hr) | MFR (g/10 min) | A-sol (%) | FM (kg/cm$^3$) |
|---|---|---|---|---|---|---|---|---|
| Example 1 | thexyltrimethoxy-silane | 5.4 | 2,3-dimethylbutyl-trimethoxysilane | 0.11 | 32,000 | 2.5 | 0.04 | 18,000 |
| Comparative Example 1 | thexyltrimethoxy-silane | 5.4 | none | — | 33,300 | 2.5 | 0.15 | 17,000 |

TABLE 1-continued

| Example No. | Component (C) Kind | Amount (mg) | Component (D) Kind | Amount (mg) | Polymerization Activity (g/g·hr) | MFR (g/10 min) | A-sol (%) | FM (kg/cm³) |
|---|---|---|---|---|---|---|---|---|
| Example 2 | t-butyltrimethoxysilane | 10.3 | n-butyltrimethoxysilane | 0.20 | 12,000 | 1.3 | 0.05 | 17,500 |
| Comparative Example 2 | t-butyltrimethoxysilane | 14.8 | none | — | 13,800 | 1.5 | 0.30 | 16,600 |
| Example 3 | thexyltrimethoxysilane | 5.4 | 2,3-dimethylbutyltrimethoxysilane | 0.33 | 31,500 | 2.6 | 0.05 | 17,900 |
| Example 4 | thexyltrimethoxysilane | " | 2,3-dimethylbutyltrimethoxysilane | 0.01 | 33,600 | 2.4 | 0.05 | 17,700 |
| Example 5 | thexyltrimethoxysilane | " | 2,3-dimethylbutyltrimethoxysilane | 0.11 | 38,500 | 3.2 | 0.04 | 17,800 |
| Comparative Example 3 | thexyltrimethoxysilane | " | none | — | 38,000 | 3.5 | 0.10 | 16,800 |
| Example 6 | thexyltrimethoxysilane | " | 2,3-dimethylbutyltrimethoxysilane | 0.11 | 29,000 | 2.6 | 0.04 | 17,300 |
| Comparative Example 4 | thexyltrimethoxysilane | " | none | — | 24,000 | 2.8 | 0.17 | 16,000 |

The catalyst of the present invention and the process for producing polyolefins using the catalyst make it possible to provide polyolefins with markedly reduced low-molecular weight components, leading to economical production of highly rigid polyolefins.

Further, the process for preparing alkyltrichlorosilanes and the process for producing alkyltrialkoxysilanes, provided by the present invention, make it possible to efficiently produce alkyltrialkoxysilanes useful as external donor for the catalyst of the present invention.

While the invention has been described in detail and with reference to specific embodiments thereof, it will be apparent to one skilled in the art that various changes and modifications can be made therein without departing from the spirit and scope thereof.

What is claimed is:

1. A catalyst for olefin polymerization comprising:
   (A) a solid catalyst component comprising a titanium compound, a magnesium compound, and a halogen compound;
   (B) an organoaluminum compound;
   (C) thexyltrimethoxysilane; and
   (D) 2,3-dimethylbutyltrimethoxysilane;
   wherein the molar ratio of said compound (D) to said compound (C) is from 0.0001 to 0.1.

2. The catalyst for olefin polymerizaiton as claimed in claim 1, wherein the molar ratio of said compound (D) to said compound (C) is from 0.01 to 0.05.

* * * * *